United States Patent [19]

McConnell

[11] Patent Number: 4,669,463

[45] Date of Patent: Jun. 2, 1987

[54] ENDOTRACHEAL TUBE INJECTION SITE ADDITION

[76] Inventor: Richard B. McConnell, 7551 SE. Thompson Ct., Milwaukie, Oreg. 97701

[21] Appl. No.: 816,674

[22] Filed: Jan. 2, 1986

Related U.S. Application Data

[63] Continuation-in-part of Ser. No. 582,345, Feb. 22, 1984, abandoned.

[51] Int. Cl.⁴ ............................................. A61M 16/00
[52] U.S. Cl. ................................ 128/207.14; 604/283; 604/256; 604/86
[58] Field of Search ............. 128/207.15, 912, 207.14, 128/207.16; 604/102, 283, 167, 256, 83, 86, 905

[56] References Cited

U.S. PATENT DOCUMENTS

| | | | |
|---|---|---|---|
| 374,831 | 12/1887 | Harrington | 128/207.14 |
| 3,022,219 | 5/1977 | Basta . | |
| 3,461,877 | 8/1969 | Morch | 128/207.14 |
| 3,683,931 | 8/1972 | Chelucci et al. | 128/207.16 |
| 3,827,729 | 8/1974 | Kamen . | |
| 3,882,862 | 5/1975 | Berend | 604/175 |
| 3,916,903 | 11/1975 | Pozzi | 604/164 |
| 3,994,293 | 11/1976 | Ferro | 604/83 |
| 4,018,231 | 4/1977 | Wallace | 128/207.15 |
| 4,121,585 | 10/1978 | Becker, Jr. | 604/86 |
| 4,152,017 | 5/1979 | Abramson . | |
| 4,240,417 | 12/1980 | Holever | 128/912 |
| 4,416,273 | 11/1983 | Grimes | 604/283 |
| 4,475,548 | 10/1984 | Muto | 128/912 |
| 4,584,998 | 4/1986 | McGrail | 604/102 |
| 4,585,435 | 4/1986 | Vaillancourt | 604/284 |

Primary Examiner—C. Fred Rosenbaum
Assistant Examiner—Gene B. Kartchner
Attorney, Agent, or Firm—Henderson & Sturm

[57] ABSTRACT

An improved endotracheal tube apparatus (10) comprising an endotracheal tube unit (11) and an injection site adjunct unit (12) wherein the tube unit (11) is provided with a primary endotracheal tube passageway (14) in communication with a respirator (100), and a lumen side port (16) formed in the wall (15) of the primary tube passageway, wherein the lumen side port (16) is in open fluid communication with the injection site adjunct unit (12) and the interior of the passageway (14) whereby liquid medicants may be introduced into the passageway.

3 Claims, 4 Drawing Figures

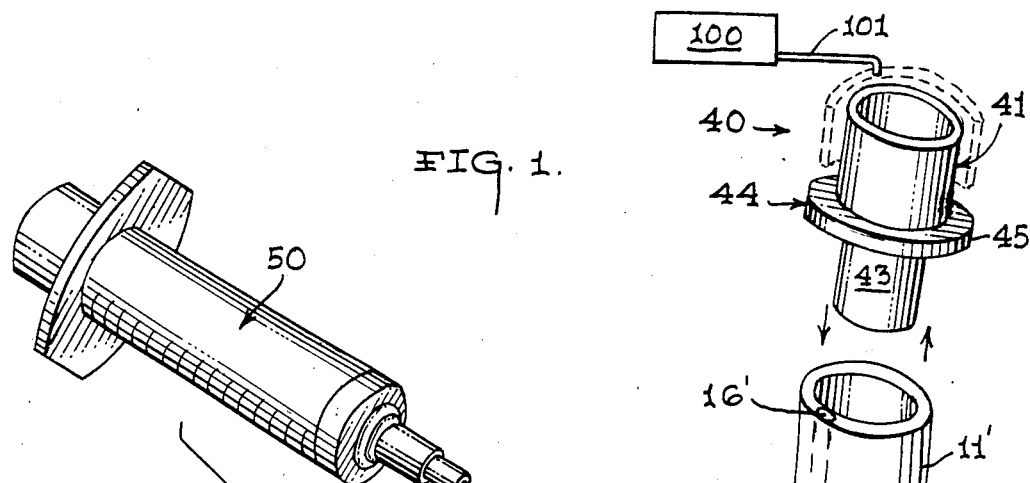
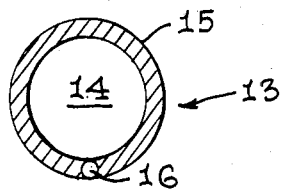
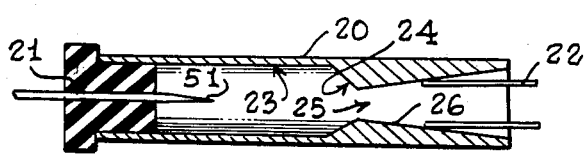
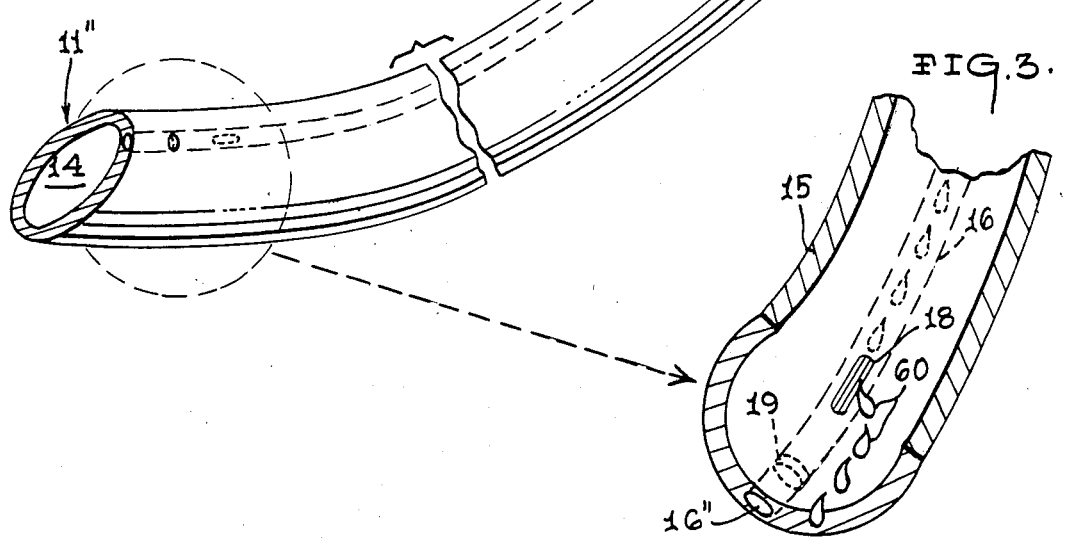

4,669,463

ENDOTRACHEAL TUBE INJECTION SITE ADDITION

This is a continuation-in-part application of Ser. No. 582,345, filed Feb. 22, 1984, now abandoned.

TECHNICAL FIELD

This invention relates generally to the field of medicine, and more specifically to endotracheal tube constructions.

BACKGROUND OF THE INVENTION

The prior art contains many examples of branched endotracheal tubes; which include U.S. Pat. Nos. 4,416,273; 4,475,548; 3,683,931; and 3,461,877. These prior art devices however, are inappropriate for the objectives of the instant invention, which is specifically directed to the introduction of liquid medicants into a closed environment, in a slow and uniform fashion.

U.S. Pat. No. 4,475,548 merely deals with a device that fits into an endotracheal tube to allow an endoscopic tube or the like to be attached to it, and which introduces the system liquid directly into the air.

U.S. Pat. No. 3,461,877 is a swivel-type tracheostomy tube. The primary purpose and function of this invention is to provide easier rotation and insertion of the tubing.

Chelucci et al, in U.S. Pat. No. 3,683,931 deals with a device which enables a patient with a tracheotomy tube to speak.

U.S. Pat. No. 4,416,273 is a connector valve assembly for endotracheal tubes. This device is connected to a conventional endotracheal tube to allow catheters to be attached. However, this invention does not provide a constant, even flow of liquid medicants into the air just before reaching the patient.

While all of the aforementioned devices are adequate for their intended purpose, they are neither designed, intended, nor adapted to be modified, to fulfill the objectives of the instant invention, which are the uniform and constant introduction of liquid medicants at the terminal end of a closed environment, while maintaining the integrity of the environment.

SUMMARY OF THE INVENTION

The instant invention provides a highly desirable alternative to the traditional endotracheal tube constructions, in that it allows liquid medicants to be injected through a self-sealing membrane and through a feeder tube into an auxiliary lumen sideport and then directly into the interior of the primary endotracheal tube, wherein the medicants exit the auxiliary tube proximate the terminus of the primary tube.

The invention in essence comprises a length of flexible feeder tubing formed integrally with the walls of an endotracheal tube and operatively connected to an auxiliary length of tubing formed as a part of the endotracheal tube wall. The wall that forms the primary endotracheal tube is of a sufficient thickness that an auxiliary lumen sideport is formed into the wall material producing primary and auxiliary passages running the length of the tube. In this manner, the liquid medicants may be introduced into the air supply very gradually and consistently. These medicants can thus be introduced to the patient without interrupting ventilation and at a point as close as possible to the location where the respirator tube terminates within the patient.

The free end of the flexible tubing is provided with a rigid cylindrical element, whose outboard end defines an enlarged opening and is further provided with a membrane element that provides an airtight seal to the assembly.

The membrane element is further adapted to be penetrated by a hypodermic needle containing liquid medicants. The material that the membrane element is fabricated from is self-sealing; so that when the needle is removed the puncture will seal to return the flexible tubing to its air tight relationship with the primary endotracheal tube.

The self-sealing aspect of the injection site allows the medicants to be introduced into a closed system, whose integrity is maintained before, during and after the penetration by a needle.

BRIEF DESCRIPTION OF THE DRAWINGS

These and other objects, advantages, and novel features of the invention will become apparent from the detailed description of the best mode for carrying out the preferred embodiment of this invention which follows; particularly when considered in conjunciton with the accompanying drawings wherein:

FIG. 1 is an enlarged perspective view of the improved endotracheal tube arrangement;

FIG. 2 is a cross-sectional view of the endotracheal tube taken through line 2—2 of FIG. 1;

FIG. 3 is an enlarged detail view of the inboard end of the endotracheal tube; and, FIG. 4 is a cross-sectional view of the injection site adjunct of the improved endotracheal tube arrangement.

BEST MODE FOR CARRYING OUT THE INVENTION

As can be seen by reference to the drawings and in particular to FIG. 1, the improved endotracheal tube apparatus that forms the basis of the present invention is designated generally by the reference numeral (10). The apparatus (10) comprises in general an endotracheal tube unit (11) and an injection site adjunct unit (12). Each of these units will now be described in seriatim fashion.

The endotracheal tube unit (11) comprises an elongated flexible endotracheal tube member (13) comprising a primary endotracheal tube passageway (14) formed by the wall (15) of the tube member (13); and, a lumen side port (16) formed in the wall (15) of the tube member (13).

As shown in FIGS. 1 thru 3, lumen side port (16) is radially off-set from the primary endotracheal tube passageway (14) and is disposed in parallel fashion along the axial length of the endotracheal tube passageway (14). In addition the lumen side port (16) is further provided with an exterior inlet port (17), an interior outlet port (18), and at least one plug element (19) whose purpose and function will be described in greater detail further on in the specification.

The injection site adjunct unit (12) is best depicted in FIGS. 1 and 4, and comprises in general an elongated hollow rigid receptacle member (20) sealingly engaged on its free end by a resilient membrane element (21), and having its inboard end engaged in fluid tight relationship with a relatively short length of narrow flexible tubing (22).

As viewed from left to right in FIG. 4, it can be seen that the interior of the hollow rigid receptacle member

(20) progresses from a generally cylindrical inlet portion (23) to an inwardly tapered conical shoulder portion (24) which defines a narrow fluid port (25) to an outwardly flared outlet portion (26).

The membrane element (21) normally sealingly engages the inlet portion (21) of the receptacle member (20); however, the membrane material is chosen such that it is self-sealing relative to the penetration and withdrawal of a hypodermic needle (50) in a well recognized manner.

As mentioned previously, the narrow flexible tubing (22) is engaged with the rigid receptacle member (20) in fluid tight fashion. This engagement may be accomplished by any suitable means such as adhesives or the like; however, as shown in FIG. 4 it is imperative for the proper functioning of this invention that the narrow fluid port (25) and the inlet of the flexible tubing (22) be axially aligned.

The aforementioned axial alignment is produced by the self-centering engagement of the flexible tubing (22) with the outwardly flared outlet portion (26) of the rigid receptacle member (20). It should also be noted that the outwardly flared outlet portion (26) of the receptacle member (20) will produce the same type of self-centering cooperation with flexible tubing (22) having larger and smaller diameters than the tubing illustrated in FIG. 4.

The internal construction of the rigid receptacle member (20) was specifically developed to maintain the closed system integrity of the apparatus when operatively deployed by virtually eliminating the possibility that the pointed end (51) of the hypodermic needle (50) could puncture the wall of the flexible tubing (22) under normal conditions.

If the penetration of the needle point (51) through the membrane element (21) occurs at an angle, or off to the side of the cylindrical inlet portion (23) of the receptacle member (20) the path of travel of the needle point (51) will be redirected by engagement with the conical shoulder portion (24) to align the needle opening with the narrow fluid port (25). In this manner the liquid medicants contained within the hypodermic needle (50) may be introduced directly into the inlet end of the flexible tubing (22).

Again referring to FIG. 1, it can be seen that the outboard end (11') of the endotracheal tube member (13) is provided with an adaptor element (40) that operatively connects the apparatus (10) to a respirator (100). The adaptor element (40) comprises a generally cylindrical member (41) having an enlarged diameter outboard section (42), a reduced diameter inboard section (43) and a transition section (44) in the form of a lip (45).

The outboard section (42) of the adaptor (40) is dimensioned to frictionally engage the outlet of a respirator tube (101) (shown in phantom). The inboard section (43) of the adaptor (40) is dimensioned to frictionally engage the interior of endotracheal tube passageway (14).

As can best be seen by reference to FIG. 3, the apparatus (10) is provided with a plug element (19) which seals the lumen side port (16) proximate the outlet end (16"), and adjacent the interior outlet port (18). The plug element (19) forces liquid medicants, which are introduced through the adjunct unit (12) and subsequently through the exterior inlet port (17) and the lumen side port (16) to flow through the interior outlet port (18) into the endotracheal tube passageway (14).

The point where the liquid medicants (60) enter the endotracheal tube passageway (14) is specifically chosen such that the medicants (60) will be introduced into the patient with an aersol dispersion providing the smallest surface area of the interior wall (15) on which aersol might stick, while still taking advantage of the suction assist created by the passage of the respiratory gases across the interior outlet port (18).

It should further be noted that the introduction of the medicants (60) through the endotracheal tube passageway (14) is not merely a matter of choice, that could just as easily be accomplished by leaving the outlet end (16") of the lumen side port unobstructed and eliminating the interior outlet port (18), so that the medicants would flow through the lumen side port outlet (16").

In the arrangement just described there is a high probability that the outlet (16") of the lumen side port (16) would be blocked or restricted by contact with the patients windpipe. Another potential problem with this arrangement is that the fluid vortex surrounding the inboard end (11") of the endotracheal tube member (13) would delay the liquid medicants from reaching their intended destination.

It should be appreciated at this juncture that the apparatus (10) that comprises the subject matter of this invention allows respiratory gases and liquid medicants to be administered to a patient simultaneously, while maintaining a closed system for the respiratory gases. In addition, cardio-pulmonary resuscitation (CPR) can be performed concurrently with the employment of the apparatus (10). It should further be noted that the introduction of the liquid medicants proximate the outlet end of the endotracheal tube passageway minimizes the amount of medicant "blow-back" into the tube passageway upon exhalation by the patient.

Having thereby described the subject matter of this invention it should be obvious that many substitutions, modifications and variations of the invention are possible in light of the above teachings. It is therefore to be understood that the invention as taught and described herein is only to be limited to the extent of the breadth and scope of the appended claims.

I claim:

1. An improved endotracheal tube apparatus used in combination with a hypodermic needle containing liquid medicants and a respirator wherein the apparatus comprises:

an endotracheal tube unit comprising an elongated flexible endotracheal tube member operatively connected on one end to the respirator, and comprising a primary endotracheal tube passageway in open communication with the respirator, and a lumen side port formed in the wall of the tube member, and extending along the axial length of the primary endotracheal tube passageway; and, an injection site adjunct unit operatively connected to said lumen side port and provided with a resilient membrane element whereby said hypodermic needle may penetrate the resilient membrane element to introduce the liquid medicants into said lumen side port; wherein, said lumen side port is further provided with: an exterior inlet port in communication with said injection site adjunct unit; an interior outlet port in communication with said primary endotracheal tube passageway; and, a plug element intermediate the inboard end of said endotracheal tube member and the said interior outlet port; wherein, the said exterior inlet port is disposed proximate the outboard end of the endotracheal tube member and said interior outlet port is disposed proximate the inboard end of the endotracheal tube member.

2. The apparatus as in claim 1; wherein, the injection site adjunct unit further comprises an elongated hollow receptacle member sealingly engaged on its free end by said resilient membrane elements, and engaged on its inboard end in a fluid tight relationship by a length of tubing, which is operatively connected to said exterior inlet port of said lumen side port.

3. The apparatus as in claim 2; wherein said receptacle member is provided with: a generally cylindrical inlet portion; an inwardly tapered shoulder portion defining a narrow fluid port; and, an outwardly flared outlet portion, which is sealingly engaged by said flexible tubing.

* * * * *